(12) United States Patent
Takahashi et al.

(10) Patent No.: US 7,936,518 B2
(45) Date of Patent: May 3, 2011

(54) HEAD-UP DISPLAY APPARATUS

(75) Inventors: Yuichi Takahashi, Niigata (JP); Keiichi Nagano, Niigata (JP); Maiko Ohdaira, Niigata (JP)

(73) Assignee: Nippon Seiki Co., Ltd., Niigata (JP)

( * ) Notice: Subject to any disclaimer, the term of this patent is extended or adjusted under 35 U.S.C. 154(b) by 0 days.

(21) Appl. No.: 12/516,463

(22) PCT Filed: Oct. 11, 2007

(86) PCT No.: PCT/JP2007/069802
§ 371 (c)(1),
(2), (4) Date: May 27, 2009

(87) PCT Pub. No.: WO2008/068956
PCT Pub. Date: Jun. 12, 2008

(65) Prior Publication Data
US 2010/0067118 A1    Mar. 18, 2010

(30) Foreign Application Priority Data
Nov. 27, 2006 (JP) .................................. 2006-317888

(51) Int. Cl.
*G02B 27/14* (2006.01)
(52) U.S. Cl. ........................................ 359/630; 359/633
(58) Field of Classification Search .................. 359/630, 359/633
See application file for complete search history.

(56) References Cited

U.S. PATENT DOCUMENTS

| 5,734,357 | A | 3/1998 | Matsumoto | |
|---|---|---|---|---|
| 6,504,518 | B1 * | 1/2003 | Kuwayama et al. | 345/7 |
| 7,111,939 | B2 * | 9/2006 | Cok et al. | 353/7 |

FOREIGN PATENT DOCUMENTS

| JP | 60-183238 | 9/1985 |
|---|---|---|
| JP | 6-247184 | 9/1994 |
| JP | 8-156646 | 6/1996 |
| JP | 2003-344801 | 12/2003 |

\* cited by examiner

*Primary Examiner* — Ricky L Mack
*Assistant Examiner* — James C Jones
(74) *Attorney, Agent, or Firm* — McDermott Will & Emery LLP

(57) ABSTRACT

A head-up display apparatus includes an infrared ray emitting unit for emitting an infrared ray toward a user, a mirror member for reflecting visible light emitted from a display toward a combiner member, and transmitting the infrared ray reflected by the user and the combiner member, a plurality of imaging units disposed to face the mirror member for sensing the infrared ray, each imaging the user from differing directions, and an image processing unit for calculating the eye position of the user based on an image captured by the imaging units.

8 Claims, 4 Drawing Sheets

HEAD-UP DISPLAY APPARATUS

RELATED APPLICATIONS

This application is the U.S. National Phase under 35 U.S.C. §371 of International Application No. PCT/JP2007/069802, filed on Oct. 11, 2007, which in turn claims the benefit of Japanese Application No. 2006-317888, filed on Nov. 27, 2006, the disclosures of which Applications are incorporated by reference herein.

TECHNICAL FIELD

The present invention relates to a head-up display apparatus configured so that visible light emitted from display means is reflected toward a user by a combiner member, forming a display image, and particularly, to form a structure for accurately calculating an eye position of the user.

BACKGROUND ART

Usually, as this kind of head-up display apparatus, one described in Patent Document 1 below has been known. With such a head-up display apparatus, it is also possible to use a combiner, and a reflecting member, of the head-up display apparatus in imaging a user by disposing an imaging device which captures an image of the user in the optical axis of the head-up display apparatus, thereby to reduce the number of dedicated members required for the imaging, captures an image of the user (particularly the user's face) with a simpler configuration, and calculate an eye position of the user. A result of the determination of the user's eye position is applicable not only to a display image position adjustment disclosed in Patent Document 1, but to a detection of a line or point of sight of the user and a determination of a condition of the user such as looking aside or falling asleep while driving.

Patent Document 1: JP-A-8-156646

DISCLOSURE OF THE INVENTION

Problems that the Invention is to Solve

However, with the previously described head-up display apparatus in Patent Document 1, a single imaging device is simply provided in an optical unit, so that there has been a problem in that a position detection accuracy, particularly in a front-rear direction of a vehicle, is low, and it is difficult to accurately calculate the user's eye position.

The invention, focusing on the previously described problem, has an object of providing a head-up display apparatus having a structure capable of capturing an image of a user and which can accurately calculate the user's eye position.

Means for Solving the Problems

In order to solve the previously described problem, the invention, being a head-up display apparatus configured so that visible light emitted from display means is reflected toward a user by a combiner member, forming a display image, is characterized by including infrared ray emitting means, which emits an infrared ray toward the user, a mirror member, which reflects the visible light, emitted from the display means, toward the combiner member, and transmits the infrared ray reflected by the user and the combiner member, a plurality of imaging means, which sense the infrared ray transmitted through the mirror member, and each image the user from different directions, and image processing means, which calculates the user's eye position based on an image captured by the imaging means.

Also, the invention is characterized in that the infrared ray emitting means is disposed in such a way as to face the mirror member, and is positioned between the plurality of imaging means.

Also, the invention is characterized in that a light shielding member is disposed between the infrared ray emitting means and the plurality of imaging means.

Also, the invention is characterized in that the light shielding member is disposed in such a way as to come into contact with the mirror member.

Also, the invention is characterized in that the mirror member is configured of a cold mirror.

Also, the invention is characterized in that the combiner member is configured of a windshield of a vehicle.

Also, the invention is characterized in that the combiner member is configured of a concave mirror disposed on a dashboard of the vehicle.

Also, the invention, including adjustment means which can adjust a position of formation of the display image, is characterized in that the adjustment means, based on a result of the calculation by the image processing means, adjusts the display image formation position.

Advantage of the Invention

The invention relates to a head-up display apparatus in which visible light emitted from display means is reflected toward a user by a combiner member to form a display image, and has a structure capable of capturing an image of the user, enabling the user's eye position to be accurately calculated.

DESCRIPTION OF REFERENCE NUMERALS AND SIGNS

Figure 1:
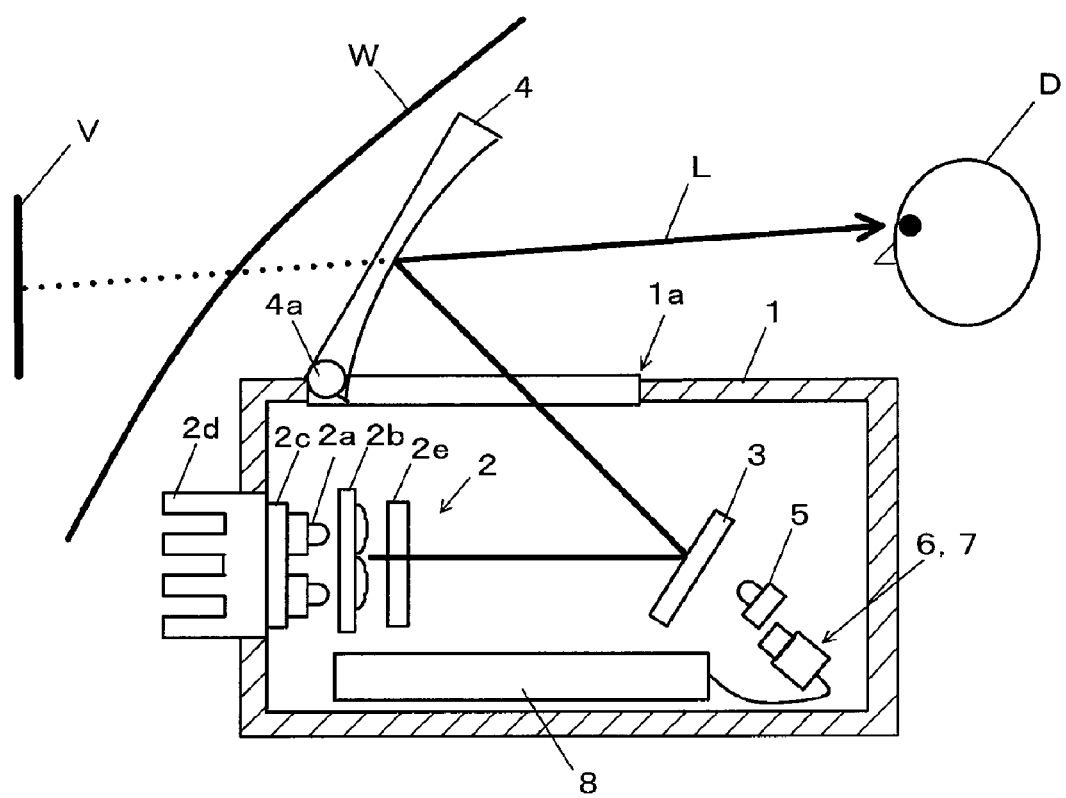
[FIG. 1] A schematic diagram of a head-up display apparatus which is an embodiment of the invention.

1 Housing
2 Display means
3 Cold mirror (mirror member)
4 Concave mirror (combiner member)
5 Infrared ray emitting means
6 First imaging means
7 Second imaging means
8 Image processing means
9 Light shielding member
D Driver (user)
L Display light (visible light)
R1 Infrared ray
R2 Infrared ray
V Virtual image (display image)
W Windshield

BEST MODE FOR CARRYING OUT THE INVENTION

Hereafter, a description will be given, based on the accompanying drawings, of embodiments of the invention.

Hereafter, a description will be given, based on the accompanying drawings, of a head-up display apparatus which is an embodiment of the invention.

Figure 2:
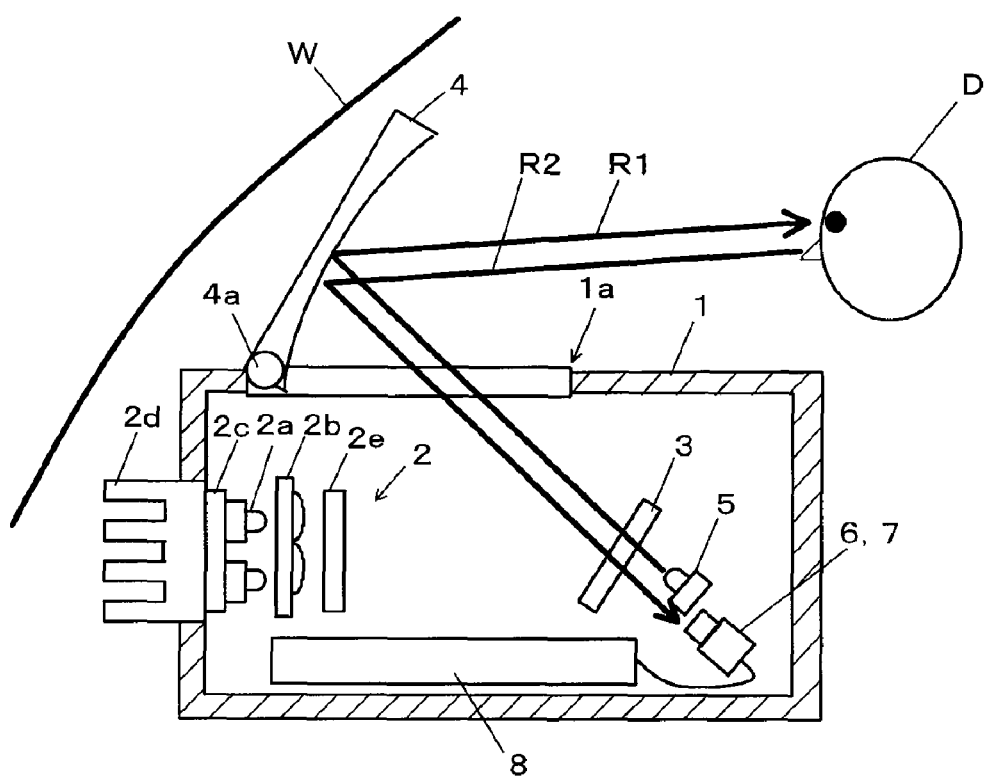
[FIG. 2] A schematic diagram of the head-up display apparatus.

As shown in FIGS. 1 and 2, the head-up display apparatus is configured mainly of a housing 1, display means 2, a cold mirror (a mirror member) 3, a concave mirror (a combiner member) 4, infrared ray emitting means 5, first imaging means 6, second imaging means 7, and image processing means 8.

With such a head-up display apparatus, as shown in FIG. 1, by display light (visible light) L emitted from the display means 2 being reflected by the concave mirror 4, and directed to a driver (a user) D, a virtual image (a display image) V is formed in such a way as to be positioned at a front of a vehicle (on a windshield W side). Also, with such a head-up display apparatus, as shown in FIG. 2, an infrared ray R1 emitted from the infrared ray emitting means 5 is transmitted through the cold mirror 3, is also reflected by the concave mirror 4, and directed to the driver D, and furthermore, an infrared ray R2 reflected off the driver D is reflected toward the cold mirror 3 by the concave mirror 4, is transmitted through the cold mirror 3, and applied to the first and second imaging means 6 and 7, thereby imaging the driver D (particularly his or her face). Consequently, it is possible to carry out an imaging of the driver D utilizing the optical path of the head-up display apparatus, and to image the driver D with a simpler configuration.

The housing 1, being made of an opaque synthetic resin material, is provided with an opening 1*a* through an upper portion thereof (on the windshield W side) in a position in which the concave mirror 4 is disposed.

The display means 2, being disposed in the housing 1, has visible light LED's 2*a*, a lens array 2*b*, a wiring substrate 2*c*, a heat radiating member 2*d*, and a liquid crystal display element 2*e*.

The visible light LED's 2*a* such as chip LED's are mounted on a surface of the wiring substrate 2*c* on the lens array 2*b* side. Also, the visible light LED's 2*a* with a low directivity (in the embodiment, 20 to 30 degrees), are respectively provided in each of positions corresponding to spherical surfaces of the lens array 2*b*. In this case, for the visible light LEDs 2*a*, two of which glow white are used.

The lens array 2*b*, being made of a transmissive synthetic resin material (for example, an acrylic resin), is provided in the housing 1. The lens array 2*b*, being configured forming a plurality of similar convex spherical surfaces (convexities) corresponding to the individual visible light LED's 2*a*, causes illumination lights from the visible light LED's 2*a* to be refracted by the spherical surfaces, enabling a visible light L with evenness to be applied to the liquid crystal display element 2*e* which is an illuminated member.

The wiring substrate 2*c*, preferably, an aluminum substrate with a high thermal conductivity, is provided on a rear side of the liquid crystal display element 2*e* inside the housing 1 in such a way as to be parallel with a predetermined distance to the lens array 2*b*. The wiring substrate 2*c*, on which are mounted electronic parts such as at least the visible light LED's 2*a*, is provided with wiring for supplying power to the electronic parts. The predetermined distance varies depending on the directivity of the visible light LED's 2*a* and the shape of the spherical surfaces of the lens array 2*b*, and such a distance as causes less unevenness in luminance is selected.

The heat radiating member 2*d*, preferably, a metal material with a high thermal conductivity, is disposed in such a way as to come into contact with the wiring substrate 2*c*, and have one portion thereof exposed outside the housing 1. The heat radiating member 2*d* has a function of radiating heat generated by a drive of the visible light LED's 2*a* to the exterior.

The liquid crystal display element 2*e* is configured so that a color filter having a red layer, a green layer, and a blue layer which are provided depending on a number of display pixels is disposed on the front surface of a liquid crystal cell having liquid crystal sealed between a pair of transmissive substrates. Also, polarizing films (polarizing members) are attached to the front and rear surfaces of the liquid crystal display element 2*e*. The liquid crystal display element 2*e*, being provided in the housing 1, is provided in a position in which illumination lights from the visible light LED's 2*a* provided behind the liquid crystal display element 2*e* reach via the lens array 2*b*. The illumination lights transmitted through the liquid crystal display element 2*e* are emitted to the cold mirror 3 as the display light L. With the liquid crystal display element 2*e*, it is possible to indicate vehicle speed and engine speed measurements as numeric values by means of, for example, a calculation circuit (not shown), which measures a vehicle speed and engine speed based on output signals from a vehicle speed sensor and engine rotation sensor provided in the vehicle, and a liquid crystal drive circuit (not shown), which drives liquid crystal based on results of the calculation. For the liquid crystal display element 2*e*, in the embodiment, a TFT type is applied, and a full color display is possible.

The cold mirror 3, being configured of a glass substrate and a reflecting film formed on a surface of the glass substrate by vapor deposition, is provided tilted at a predetermined angle to the optical axes of the visible light LED's 2*a*. The reflecting film of the cold mirror 3 has a property of transmitting only an infrared ray, and reflecting a visible light ray and an ultraviolet ray. That is, the display light L transmitted through the liquid crystal display element 2*e* is reflected toward the concave mirror 4 by the cold mirror 3. Also, by using the cold mirror 3, the infrared ray R2 caused to fall incident inside the housing 1 from the exterior is transmitted through the cold mirror 3, and directed to the first and second imaging means 6 and 7 (refer to FIG. 2).

The concave mirror 4, provided corresponding to the opening 1*a* in the housing 1, which reflects the display light L, projected via the liquid crystal display element 2*e* and cold mirror 3, to the driver D side, is provided so as to be angle adjustable by angle adjustment means 4*a* (adjustment means) configured of an not-shown motor, gear, and the like in such a way that the driver D easily visually perceives the display light L. A position in which the virtual image V is formed can be adjusted by rotating the concave mirror 4 by means of the angle adjustment means 4*a*. Also, the concave mirror 4 is formed of a reflecting surface having a predetermined curvature in order that the display light L is displayed enlarged. Also, the concave mirror 4 reflects the infrared ray R1, emitted from the infrared ray emitting means 5, toward the driver D, and furthermore, reflects the infrared ray R2, reflected by the user D, toward the first and second imaging means 6 and 7 (refer to FIG. 2).

Figure 3:
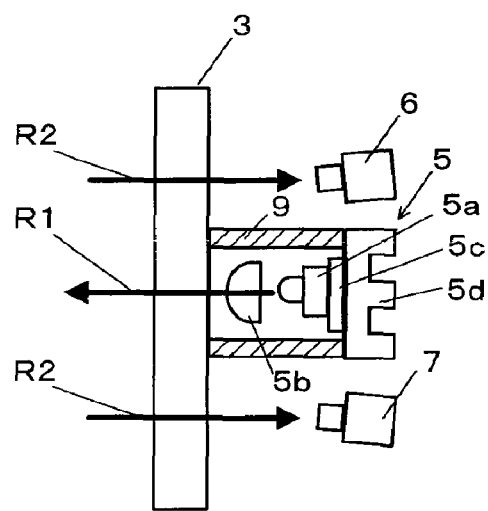
[FIG. 3] A diagram showing infrared ray emitting means, and first and second imaging means, of the head-up display apparatus.

The infrared ray emitting means 5, emitting the infrared ray R1 toward the concave mirror 4, is disposed in the housing 1 in such a way as to face the concave mirror 4 across the cold mirror 3. As shown in FIG. 3, the infrared ray emitting means 5 has an infrared LED 5*a* emitting an infrared ray, a collective lens 5*b* made of a convex resin material, a circuit substrate 5*c*, and a heat radiating member 5*d*. The infrared ray emitted from the infrared LED 5a, the distribution of which is controlled by the collective lens 5b, is transmitted through the cold mirror 3, and emitted toward the concave mirror 4. The circuit substrate 5c and heat radiating member 2d are made of a metal material with a high thermal conductivity in order to radiate heat generated by a drive of the infrared LED 5a to the exterior.

The first and second imaging means 6 and 7, each of which is configured of a CCD camera or the like which senses an infrared ray, and captures an image (in the embodiment, a facial image of the driver D), are disposed in the housing 1 in such a way as to face the concave mirror 4 across the cold mirror 3, as well as to surround the infrared ray emitting means 5. By the infrared ray emitting means 5 being disposed in such a way as to be positioned between the first and second imaging means 6 and 7, it is possible to increase a distance between the first and second imaging means 6 and 7, and it is possible to improve the accuracy with which is detected an eye position of the driver D, to be described hereafter.

Also, as shown in FIG. 3, a light shielding member 9 is disposed between the infrared ray emitting means 5 and the first and second imaging means 6 and 7. The light shielding member 9, being made of, for example, a cylindrical metal material, shields the infrared ray R1 so that the infrared ray R1 emitted from the infrared LED is not directly sensed by the first and second imaging means 6 and 7. For this reason, the light shielding member 9, being disposed in such a way as to come into contact with the cold mirror 3, has a configuration such that no clearance is formed between itself and the cold mirror 3. By providing the light shielding member 9, it is possible to prevent the infrared LED 5a from being directly imaged by the first and second imaging means 6 and 7, and by housing the infrared ray emitting means 5 in the housing 1, a simple configuration is possible wherein no special attachment is necessary, and it is possible to efficiently carry out capturing a image of the driver D.

The image processing means 8, being disposed in the housing 1, is electrically connected to the first and second imaging means 6 and 7. The image processing means 8 receives facial images of the driver D captured in different directions from the first and second imaging means 6 and 7, and calculates an eye position of the driver D from such a plurality of facial images. By calculating the eye position of the driver D based on the facial images from the plurality of differing angles in such a way, it is also possible to accurately calculate the eye position in a front-rear direction of the vehicle. A result of the calculation of the eye position of the driver D is transmitted to not-shown control means. The control means has a function of driving the angle adjustment means 4a, for example, based on such a calculation result, making an automatic adjustment in such a way that the virtual image V is positioned so as to be well visible to the driver D. The function utilizing the eye position calculation result is not limited to the heretofore described virtual image V formation position adjustment.

Figure 4:
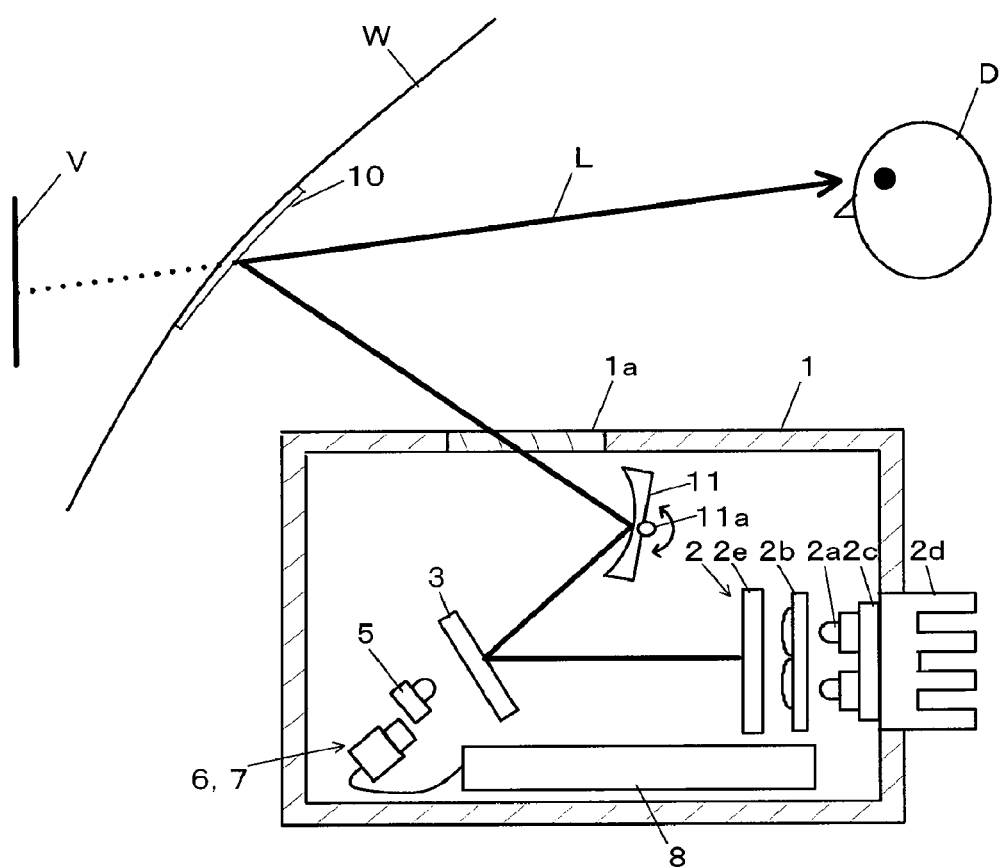
[FIG. 4] A schematic diagram of a head-up display apparatus which is another embodiment of the invention.
Figure 5:
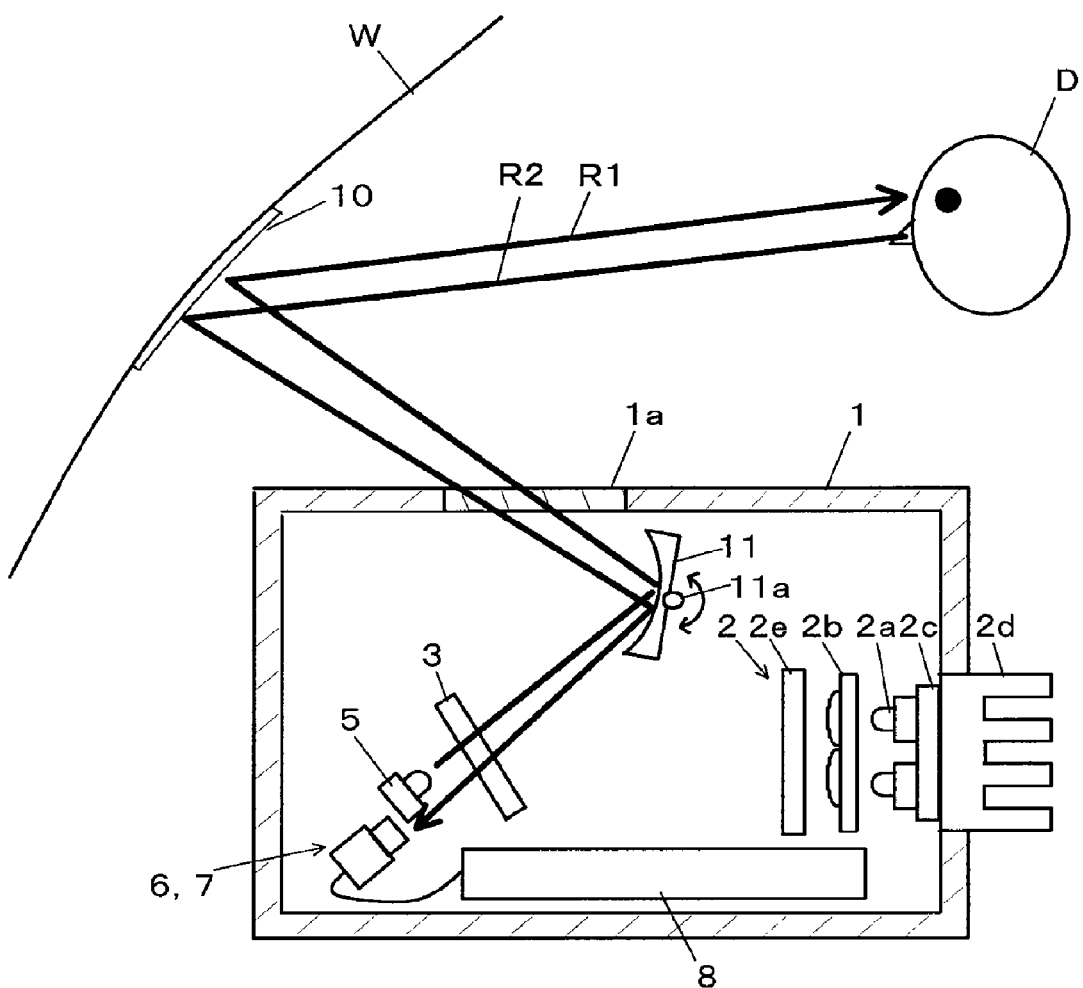
[FIG. 5] A schematic diagram of the head-up display apparatus.

FIGS. 4 and 5 are diagrams showing other embodiments of the invention. A difference from the heretofore described embodiment is that the combiner member reflecting the display light L and the infrared rays R1 and R2 is configured of a windshield W on which a multilayer film 10 is formed. It is also possible to obtain the advantages of the invention with such a configuration. Reference numeral 11 showing a concave mirror which reflects the display light L and the infrared ray R1 toward the windshield W, and reflects the infrared ray R2, caused to fall incident from the exterior, toward the first and second imaging means 6 and 7, the concave mirror 11 is provided so as to be angle adjustable by angle adjustment means 11a (adjustment means) configured of an not-shown motor, gear, and the like in such a way that the driver D easily and visually perceives the display light L. It is possible to adjust the virtual image V formation position by rotating the concave mirror 11 by means of the angle adjustment means 11a. Also, the multilayer film 10 is formed as appropriate in order to make an adjustment in such a way that the reflection of the display light L and infrared ray R1 is efficiently carried out.

INDUSTRIAL APPLICABILITY

The invention relating to a structure for accurately calculating an eye position of the user, a result of the calculation of the user's eye position is applicable not only to the display image position adjustment of each of the embodiments, but to a detection of a line or point of sight of the user, and a determination of a condition of the user such as inattentiveness or drowsiness.

The invention claimed is:

1. A head-up display apparatus configured to reflect visible light emitted from display means toward a user by a combiner member to form a display image, the head-up display apparatus comprising:
   infrared ray emitting means for emitting an infrared ray toward the user;
   a mirror member for reflecting the visible light emitted from the display means toward the combiner member, and transmitting the infrared ray reflected by the user and the combiner member;
   a plurality of imaging means for sensing the infrared ray transmitted through the mirror member, and each imaging the user from differing directions; and
   image processing means for calculating the user's eye position based on an image captured by the imaging means,
   wherein the infrared ray emitting means is disposed to face the mirror member and be positioned between the plurality of imaging means.

2. A head-up display apparatus configured to reflect visible light emitted from display means toward a user by a combiner member to form a display image, the head-up display apparatus comprising:
   infrared ray emitting means for emitting an infrared ray toward the user;
   a mirror member for reflecting the visible light emitted from the display means toward the combiner member, and transmitting the infrared ray reflected by the user and the combiner member;
   a plurality of imaging means for sensing the infrared ray transmitted through the mirror member, and each imaging the user from differing directions; and
   image processing means for calculating the user's eye position based on an image captured by the imaging means,
   wherein a light shielding member is disposed between the infrared ray emitting means and the plurality of imaging means.

3. The head-up display apparatus according to claim 2, wherein the light shielding member is disposed to come in contact with the mirror member.

4. The head-up display apparatus according to claim 1 or 2, wherein the mirror member comprises a cold mirror.

5. The head-up display apparatus according to claim 1 or 2, wherein the combiner member comprises a windshield for a vehicle.

6. The head-up display apparatus according to claim 1 or 2, wherein the combiner member comprises a concave mirror disposed on a dashboard of the vehicle.

7. The head-up display apparatus according to claim 1 or 2, further comprising:

adjustment means for adjusting a position of formation of the display image, the adjustment means adjusting the display image formation position based on a result of the calculation by the image processing means.

8. The head-up display apparatus according to claim 1, wherein a light shielding member is disposed between the infrared ray emitting means and the plurality of imaging means.

\* \* \* \* \*